(12) United States Patent
Vargas

(10) Patent No.: US 6,905,504 B1
(45) Date of Patent: Jun. 14, 2005

(54) TOOL FOR PERFORMING END-TO-END ANASTOMOSIS

(75) Inventor: Jaime S. Vargas, Menlo Park, CA (US)

(73) Assignee: Cardica, Inc., Redwood City, CA (US)

( * ) Notice: Subject to any disclaimer, the term of this patent is extended or adjusted under 35 U.S.C. 154(b) by 323 days.

(21) Appl. No.: 10/083,235

(22) Filed: Feb. 26, 2002

(51) Int. Cl.[7] .................................................. A61B 17/03
(52) U.S. Cl. ..................................... 606/153; 227/175.1
(58) Field of Search ................................. 606/153, 219, 606/221, 149, 150; 227/175.1, 181.1, 179.1

(56) References Cited

U.S. PATENT DOCUMENTS

| | | | | |
|---|---|---|---|---|
| 1,151,300 A | * | 8/1915 | Soresi | .............................. 604/7 |
| 1,217,637 A | * | 2/1917 | Rink | ............................. 606/86 |
| 3,048,177 A | * | 8/1962 | Takaro | ......................... 606/153 |
| 3,114,367 A | * | 12/1963 | Carpenter et al. | ........... 606/151 |
| 3,254,650 A | | 6/1966 | Collito | |
| 3,254,651 A | | 6/1966 | Collito | |
| 3,265,069 A | * | 8/1966 | Healey, Jr. et al. | .......... 606/153 |
| 3,519,187 A | | 7/1970 | Kapitanov | |
| 3,774,615 A | | 11/1973 | Lim et al. | |
| 3,911,926 A | * | 10/1975 | Peters | .......................... 606/158 |
| 4,245,638 A | * | 1/1981 | Lebeck et al. | ............... 606/150 |
| 4,350,160 A | | 9/1982 | Kolesov et al. | |
| 4,523,592 A | | 6/1985 | Daniel | |
| 4,553,542 A | | 11/1985 | Schenck et al. | |
| 4,593,693 A | | 6/1986 | Schenck | |
| 4,607,637 A | | 8/1986 | Berggren et al. | |
| 4,624,255 A | | 11/1986 | Schenck et al. | |
| 4,624,257 A | | 11/1986 | Berggren et al. | |
| 4,635,636 A | * | 1/1987 | Goldstein | ................... 606/150 |
| 4,657,019 A | | 4/1987 | Walsh et al. | |
| 4,721,109 A | | 1/1988 | Healey | |
| 4,747,407 A | | 5/1988 | Liu et al. | |
| 4,907,591 A | | 3/1990 | Vasconcellos et al. | |
| 4,917,087 A | | 4/1990 | Walsh et al. | |
| 4,917,090 A | | 4/1990 | Berggren et al. | |
| 4,917,091 A | | 4/1990 | Berggren et al. | |
| 5,011,487 A | * | 4/1991 | Shichman | .................... 606/158 |
| 5,119,983 A | | 6/1992 | Green et al. | |
| 5,122,156 A | * | 6/1992 | Granger et al. | .............. 606/219 |
| 5,141,516 A | | 8/1992 | Detweiler | |
| 5,158,567 A | * | 10/1992 | Green | ......................... 606/219 |
| 5,192,289 A | | 3/1993 | Jessen | |
| 5,669,918 A | * | 9/1997 | Balazs et al. | ................ 606/139 |
| 5,702,048 A | | 12/1997 | Eberlin | |
| 6,468,285 B1 | * | 10/2002 | Hsu et al. | .................... 606/158 |

FOREIGN PATENT DOCUMENTS

| | | |
|---|---|---|
| EP | 00/15144 | 3/2000 |
| WO | WO 99/11178 | 3/1999 |

OTHER PUBLICATIONS

Wood, Michael B. Atlas of Reconstructive Microsurgery 1990 P4–5.
Lorenzetti, Fulvio Blood Flow in Free Microvascular Flaps, 2001, P5–52.

* cited by examiner

Primary Examiner—Anhtuan T. Nguyen
Assistant Examiner—Bradford C Pantuck
(74) Attorney, Agent, or Firm—Brian A. Schar

(57) ABSTRACT

A tool for performing anastomosis connects two tissue structures end-to-end. An end of each of the two tissue structures is sized to a known interface dimension with a tissue preparation device, and two or more cuts are made in that end to create at least two flaps. a clamp holds each tissue structure, and each clamp may be integrated with a tissue preparation device. The clamps are movable relative to one another, and are registered together such that the flaps of one tissue structure are pressed against the corresponding flaps of the other tissue structure when the clamps come together. Each flap of one tissue structure is connected to a corresponding flap on the other corresponding tissue structure with at least one connector such as a staple or other fastener.

16 Claims, 7 Drawing Sheets

TOOL FOR PERFORMING END-TO-END ANASTOMOSIS

FIELD OF THE INVENTION

The present invention relates generally to anastomosis, and more particularly to a tool for performing end-to-end anastomosis.

BACKGROUND

End-to-end anastomosis is a surgical procedure for connecting an end of one hollow tissue structure to an end of another hollow tissue structure, such that the spaces within each hollow tissue structure are connected. End-to-end anastomosis is commonly performed in a microvascular context. Microvascular anastomosis is performed between ends of blood vessels in the course of, for example, reattaching severed body parts and/or transplanting organs. The blood vessels connected together often have different diameters, both of which are very small, on the order of one millimeter. Microvascular anastomosis is often performed by hand under a microscope, and is tedious and painstaking work. As a result, it can take many hours to complete just the microvascular anastomosis required to reconnect a severed body part or transplant an organ.

One attempt to provide a mechanism for performing such a microvascular anastomosis is the Microvascular Anastomotic Coupler System from Bio-Vascular, Inc. In this mechanism, an end of each vessel to be connected is everted over a ring with a forceps or similar instrument. Each ring includes a number of pins over which the vessel is everted. The rings are then pressed together, such that the pins on each ring enter recesses in the other ring, connecting the rings and holding the ends of the vessels together. However, this system is limited to use with two blood vessels having substantially the same diameter. Further, manual eversion of a blood vessel having a diameter on the order of one millimeter is difficult and painstaking, particularly when the eversion is to be substantially even around the circumference of the ring. Further, the rings provide a noncompliant anastomosis between the two vessels.

SUMMARY

An anastomosis tool is used to connect two tissue structures end-to-end.

In one aspect of the invention, an end of a tissue structure is sized to a known interface dimension with a tissue preparation device. The tissue preparation device may include a pin and a measuring feature relative to the pin. The measuring feature is configured to measure the interface dimension. A tissue structure is moved relative to the pin until the measuring feature maps the interface dimension onto a cross-section of the tissue structure. The tissue structure is then held in place while two or more cuts are made in it to create at least two flaps at its end.

In another aspect of the invention, a clamp holds each tissue structure. A tissue preparation device may be integrated with each clamp. The clamps are moveable relative to one another in order to bring the flaps of one tissue structure in contact with the flaps of the other tissue structure. At least one clamp includes at least one connector deployer. Additionally, at least one clamp may include a connector receiver corresponding to a connector deployer on another clamp.

In another aspect of the invention, the flaps on each tissue structure are held by one or more clips. The clip or clips may be provided as a component of each clamp, or may be separate structures or mechanisms detachable from the clamps. By holding the flaps in a predetermined position, the flaps on different tissue structures can be brought together in a configuration suitable for connecting them together.

In another aspect of the invention, at least one clamp is movable relative to a jig. The jig guides the clamps together such that the flaps of one tissue structure are registered against the corresponding flaps of the other tissue structure. The jig may include one or more rails along which at least one clamp is configured to slide.

In another aspect of the invention, each flap of one tissue structure is connected to a corresponding flap on the other corresponding tissue structure with at least one connector. These connectors may be staples or other fasteners. The connectors are spaced apart from one another a distance comparable to the distance between stitches in a sutured anastomosis. By using a number of spaced-apart connectors such as staples, the anastomosis is compliant.

BRIEF DESCRIPTION OF THE DRAWINGS

The use of the same reference symbols in different figures indicates similar or identical items.

DETAILED DESCRIPTION

Figure 1:
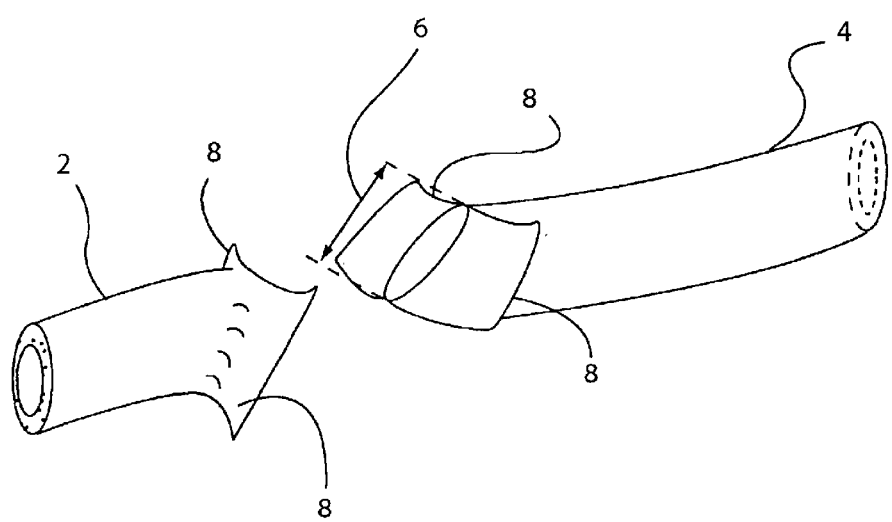
FIG. 1 is a perspective view of two tissue structures to be connected to one another.

Referring to FIG. 1, a first tissue structure 2 and a second tissue structure 4 are to be connected to one another. The tissue structures 2, 4 are hollow structures each having an end in proximity to an end of the other. The tissue structures 2, 4 may be blood vessels, ducts or other tubular structures. For example, these tissue structures 2, 4 may be small blood vessels on the order of one millimeter in diameter, such that the connection between them may be categorized as microvascular anastomosis. Such microvascular anastomosis may be used to connect tissue structures 2, 4 in the course of a transplant procedure, the reattachment of a severed limb or bodily part, or in other contexts.

The first tissue structure 2 may have a different diameter than the second tissue structure 4. Where an organ is being transplanted, the first tissue structure 2 and the second tissue structure 4 may have different diameters because each is from a different individual or from a different part of the same individual, or because a portion of a previous unitary tissue structure was destroyed or damaged. In order to connect tissue structures 2, 4 having different diameters, an interface length 6 is defined and mapped onto the end of each tissue structure 2, 4. The process of determining a cross-section of the tissue structure 2, 4 that has a width substantially equal to the interface length 6 may be referred to as mapping the interface length 6 onto the tissue structure 2, 4. The interface length 6 is defined along an angle to the centerline of each tissue structure 2, 4. The angle at which the end of each tissue structure 2, 4 is cut may be different in order to produce the same interface length 6 at the end of each tissue structure. The end of each tissue structure 2, 4 is cut along that angle, such that the end of each tissue structure 2, 4 defines a plane relative to its centerline. The diameter of the lumen of each tissue structure 2, 4 as measured in that plane is substantially the same. The tissue structures 2, 4 may be flattened while the interface length 6 is mapped onto them, such that the flattened tissue structures 2, 4 are each cut to the interface length 6. The resulting diameter of each tissue structure 2, 4 after returning to its normal, non-flattened state is thus substantially the same, and is slightly less than the interface length 6.

After anastomosis, the centerline of the first tissue structure 2 may be angled relative to the centerline of the second tissue structure 4, because the angle cut at the end of each tissue structure 2, 4 may be different. Advantageously, the interface length 6 is selected to be greater than the expected diameter of either tissue structure 2, 4, such that the end of each tissue structure 2, 4 is cut at an angle to its centerline in order to increase the surface area of the flaps 8. However, the interface length 6 instead may be selected to be closer to the expected diameter of either tissue structure 2, 4.

Figure 2:
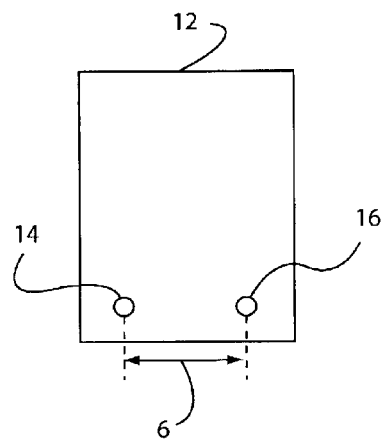
FIG. 2 is a schematic view of one configuration of a tissue preparation device.
Figure 3:
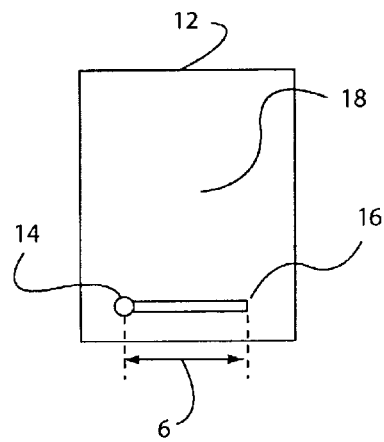
FIG. 3 is a schematic view of another configuration of a tissue preparation device.

Referring to FIG. 2, the end of each tissue structure 2, 4 is cut to a width substantially equal to the interface length 6 using a tissue preparation device 12. The tissue preparation device 12 may be integrated into a deployment tool, as described below, or may be an independent mechanism. The tissue preparation device 12 includes a pin 14 extending outward from a surface 18. Alternately, a structure other than a pin 14 could be used. The tissue preparation device 12 also includes a measuring feature 16 spaced apart from the pin 14 a distance substantially equal to the interface length 6. Referring to FIG. 2, the measuring feature 16 is another pin. Referring to FIG. 3, the measuring feature 16 is a visually-perceptible feature on the surface 18. The visually perceptible feature may be a colored strip, a set of ruled lines, or any other visible feature on the surface 18. The visually perceptible feature may be defined on, attached to or otherwise placed on the surface 18. The measuring feature 16 may be any other structure or mechanism useful in measuring the width of a tissue structure 2, 4.

Figure 4:
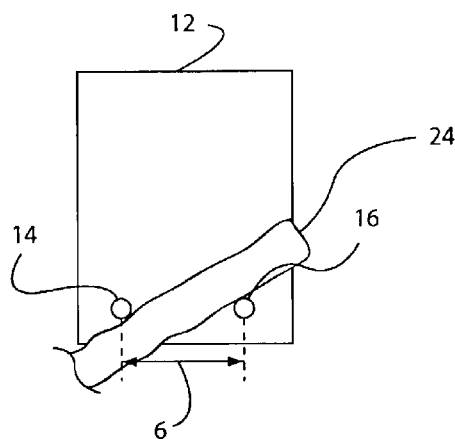
FIG. 4 is a schematic view of the tissue preparation device of FIG. 3 as used to map the interface length onto the end of a tissue structure.

Referring to FIG. 4, a tissue structure 2, 4 is measured using the tissue preparation device 12 of FIG. 2. The tissue structure 2, 4 is placed between the pin 14 and the measuring feature 16, using a forceps or other tool, or by hand. The tissue structure 2,4 is then moved relative to both the pin 14 and the measuring feature 16 such that, as viewed from the top, one side of the tissue structure 2, 4 contacts the pin 14 and the opposite side of the tissue structure 2, 4 contacts the measuring feature 16. The distance between these two points of contact is substantially equal to the interface length 6. The interface length 6 is potentially a greater distance than the width of the tissue structure 2, 4. Thus, the tissue structure 2, 4 is moved to an angle to an imaginary line connecting the pin 14 and the measuring feature 16, such that adequate tissue is present between the pin 14 and the measuring feature 16 to allow the interface length 6 to be mapped onto that tissue structure 2, 4.

Figure 5:
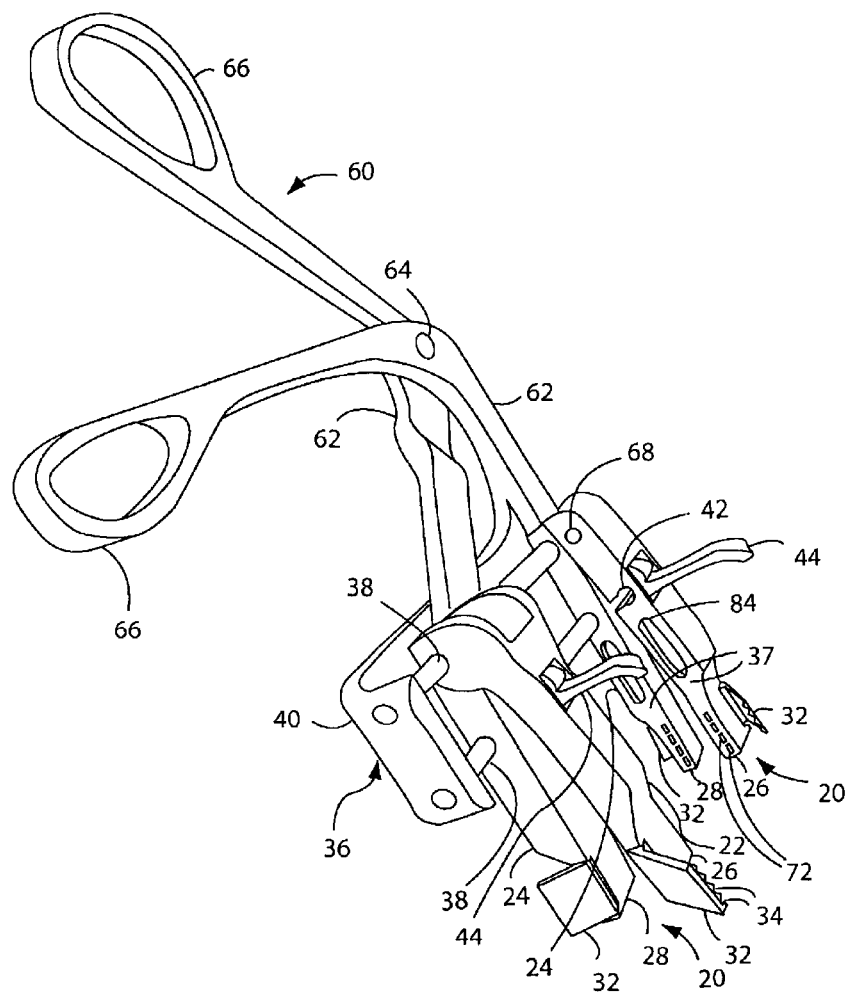
FIG. 5 is a perspective view of an anastomosis tool.

Referring to FIG. 5, an anastomosis tool 30 for performing end-to-end anastomosis is shown. The anastomosis tool 30 includes two clamps 20. Each clamp 20 includes a first arm 22 and a second arm 24. The first arm 22 has a distal end 26, and the second arm 24 has a distal end 28. The first arm 22 and the second arm 24 are both configured to rotate from an open position, in which the distal end 26 of the first arm 22 is spaced apart from the distal end 28 of the second arm 24, to a closed position, in which the distal end 26 of the first arm 22 is in proximity to the distal end 28 of the second arm 24. In the closed position, the first arm 22 and second arm 24 hold a flattened tissue structure 2, 4 between them, such that the first arm 22 is separated from the second arm 24 by the thickness of the flattened tissue structure 2, 4. Alternately, the first arm 22 and the second arm 24 are movable relative to one another in any manner as long as the first arm 22 and the second arm 24 are capable of motion between an open position and a closed position. For example, the first arm 22 and the second arm 24 may slide together to a closed position from an open position.

When in the open position, the clamp 20 is capable of receiving a tissue structure 2,4 between the first arm 22 and the second arm 24. The tissue preparation device 12 described above is positioned on the surface of the first arm 22 that faces the second arm 24, or on the surface of the second arm 24 that faces the first arm 24. Thus, the pin 14 and the measuring feature 16 are provided on a surface of one of the arms 22, 24, and recess (not shown) corresponding to the pin 14 is provided on the corresponding surface of the other arm 22, 24, such that the arms 22, 24 can close. Where the measuring feature 16 is a pin, a recess corresponding to that pin is provided in the corresponding surface of the other arm 22, 24 as well. Thus, after the interface length 6 has been mapped onto the tissue structure 2, 4, the clamp 20 can be closed, trapping and firmly holding the tissue structure 2, 4 between the first arm 22 and the second arm 24. Advantageously, each clamp 20 holds a tissue structure 2, 4 between its arms 22, 24 without penetrating the tissue structure 2, 4 in whole or in part. Instead, each clamp 20 holds a tissue structure 2, 4 by gripping it between its arms 22, 24. In this way, the tissue structure 2, 4 is not damaged by the clamps 20, and any leakage that may result from penetration of the tissue structures 2, 4 is avoided. However, one or more of the clamps 20 may penetrate a tissue structure 2, 4 in order to hold it in place. Alternately, the tissue preparation device 12 is independent from the clamp 20. If so, the ends of the tissue structures 2, 4 are cut and flaps formed in them using an independent tissue preparation device 12, after which a user moves the ends of the tissue structures 2, 4 into clamps 20 using a forceps or other tool, or by hand.

Referring also to FIG. 1, after the interface length 6 has been mapped onto the tissue structure 2, 4 and the clamp 20 is closed, flaps 8 arc cut in the end of the tissue structure 2, 4. A scissors, scalpel or other tool may be used to do so. Advantageously, two cuts are made in the walls of the tissue structure 2, 4, resulting in two flaps 8. The two cuts are made substantially one hundred and eighty degrees apart with regard to the circumference of the tissue structure, such that the flaps 8 flank the end of the lumen 10 of the tissue structure 2,4. More cuts may be made if desired, thereby resulting in more flaps.

Figure 5A:
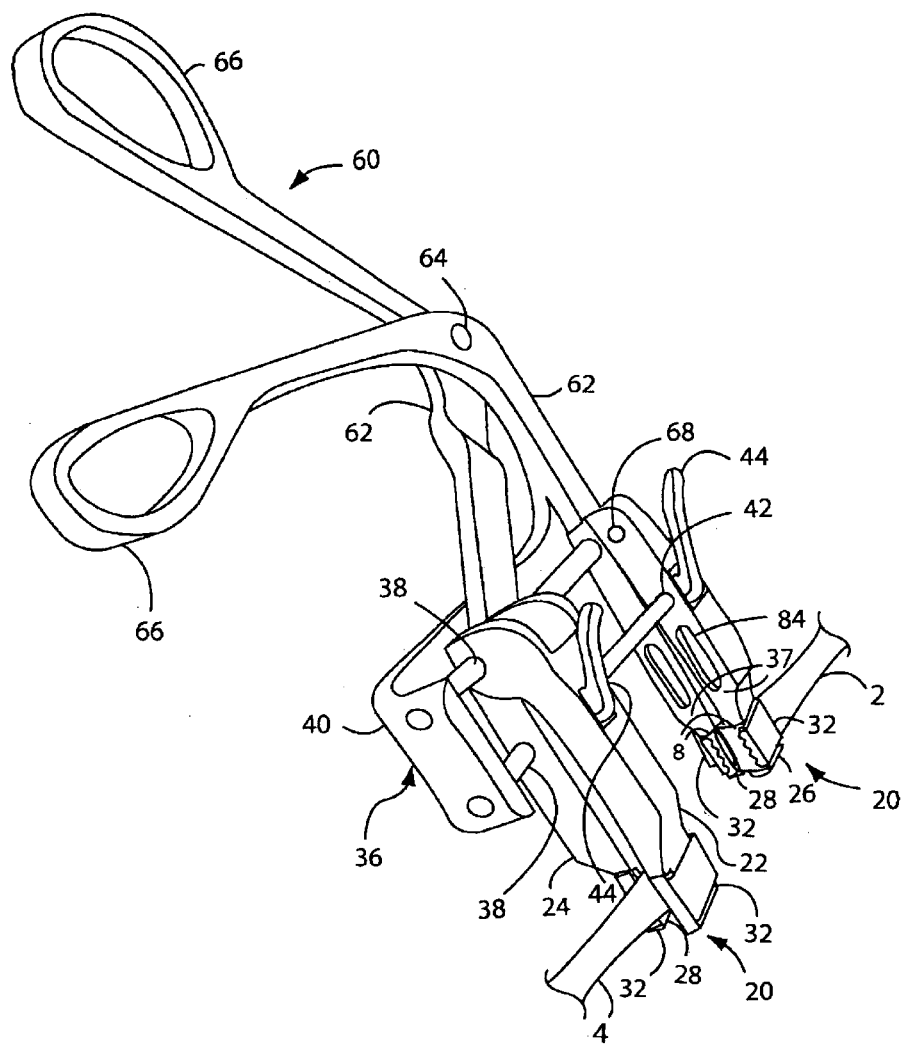
FIG. 5A is a perspective view of the anastomosis tool of FIG. 5, showing tissue structures held by clamps of the anastomosis tool and flaps of the tissue structures held by clips of the anastomosis tool.

Referring also to FIG. 5A, a tissue clip 32 is attached to each arm 22, 24 of each clamp 20. One edge of each clip 32 is attached to the surface of the corresponding arm 22, 24, and another edge of each clip 32 is free to move relative to the surface of the arm 22,24 to allow the clip 32 to move between an open position and a closed position. Each clip 32 may include a number of teeth 34 or other gripping features at its free edge, to better grip a flap 8 of the tissue structure 2, 4 between the clip 32 and the corresponding arm 22, 24. Each clip 32 is initially in an open position in order to receive the corresponding flap 8. After the flaps 8 have been created by cutting the tissue structures 2, 4, each flap 8 is pulled relative to an arm 22, 24 of a clamp 20 such that a portion of the flap 8 extends into a space between a clip 32 and a surface of the arm 22, 24. A forceps or other tool may be used to move the flap 8. Once a portion of a flap 8 is moved into the space between a clip 32 and its corresponding arm 22, 24, the clip 32 is closed. The clip 32 includes one or more features for providing firm engagement between the free end of the clip 32 and the associated arm 22, 24 in the closed position. For example, the edge of each clip 32 that is connected to a corresponding arm 22, 24 may include a cam, lock, or other feature that engages a corresponding feature in the arm 22, 24 to hold the clip 32 closed. For example, the clips 32 may lock into place in the same or similar manner as the clamping levers 44 described below. In this way, each flap 8 is held securely against an arm 22, 24 by a clip 32. Advantageously, the clips 32 hold the corresponding flaps 8 under tension, such that a portion of each flap 8 is held substantially flat against a contact surface 37 of each arm 22, 24. The contact surface 37 of each arm 22,24 is the surface that faces the corresponding arm 22, 24 of the other clamp 20. Alternately, one or more clips 32 are detachable from the clamp 20. At least one of the clips 32 may be configured to hold more than one flap 8 at a time. Such a clip 32 may be a U-shaped or C-shaped clip that extends across at least a portion of both arms 22, 24 of the clamp 20.

At least one clamp 20 is moveable relative to a jig 36, which is a component of the anastomosis tool 30. The jig 36 includes a frame 40 and two rails 38, where each rail 38 is attached at each end to the frame 40. The rails 38 are fixed to the frame 40. Alternately, the rails 38 may be moveable relative to the frame 40. The rails 38 are substantially cylindrical rods. Alternately, one or more of the rails 38 may be shaped differently. Each arm 22, 24 of each clamp 20 includes a passage defined therethrough, through which one of the rails 38 passes. The first arm 22 rotates relative to the centerline of that rail 38, thereby rotating relative to the second arm 24. The second arm 24 of each clamp 20 also includes a passage therethrough, through which a second rail 38 passes. In this way, each second arm 24 is substantially restricted to travel in a direction substantially parallel to the centerlines of the rails 38. Alternately, the arms 22, 24 are connected to the rails 38 in a different way. For example, the first arm 22 may be substantially restricted to travel in a direction substantially parallel to the centerlines of the rails 38, while the second arm 24 is free to rotate about the centerline of one of the rails 38.

Optionally, the first arm 22 of each clamp 20 includes a slot 42 defined therein. A slot 42 may be provided on one or both sides of the first arm 22. The slot 42 is positioned on the first arm 22 such that, when the clamp 20 is in a closed position, the slot 42 engages a corresponding peg (not shown) on the second arm 24. Alternately, the slot 42 engages one of the rails 38. In this way, the slot or slots 42 align the arms 22, 24. The slot 42 includes a portion having a diameter substantially the same as the corresponding peg, and a portion sized slightly narrower than the diameter of that peg, such that the slot 42 does not completely engage the peg until pressure is applied in order to force the narrow portion of the slot 42 over the diameter of the peg. Alternately, the slots 42 do not include narrow areas, and only loosely engage the peg.

Figure 6:
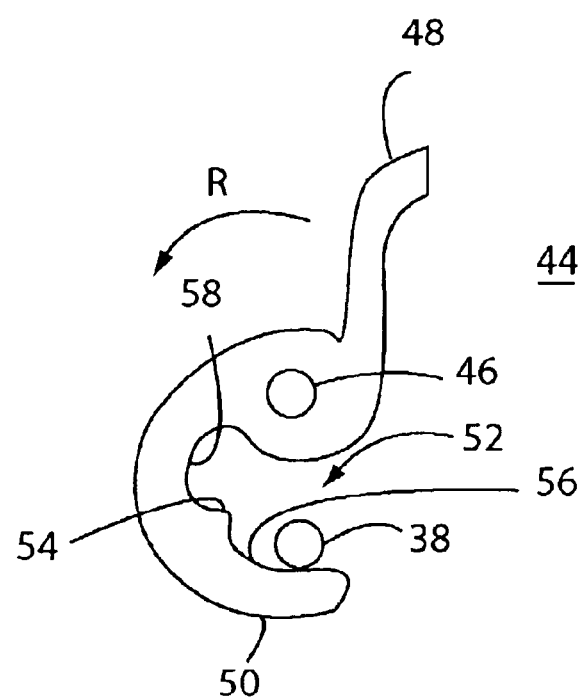
FIG. 6 is a side view of a clamping lever used as a component of the anastomosis tool.

A clamping lever 44 may also be connected to each clamp 20. Referring also to FIG. 6, the clamping lever 44 rotates around a pin 46 or other structure within the first arm 22 of each clamp 20. An interface structure 48 extends out of the first arm 22, such that a user can contact the interface structure 48 by hand or using a tool such as a forceps in order to rotate the clamping lever 44 around the pin 46. The clamping lever 44 also includes a finger 50. The finger 50 is spaced apart from the pin 46, such that a space 52 is present in the clamping lever 44 between the finger 50 and a portion of the clamping lever 44 adjacent to the pin 46. The space 52 is sized to accept a rail 38 of the jig 36. As the clamping lever 44 is rotated relative to the pin 46 in the direction R, the finger 50 moves relative to the rail 38, such that the rail 38 enters the space 52. The rail 38 may ride along an inner surface 56 of the finger 50 for at least a portion of the rotation of the clamping lever 44. The inner surface 56 may additionally have a varying radius along its length relative to the pin 46, such that the finger 50 contacts and exerts increasing force on the rail 38 during its rotation. As the clamping lever 44 continues to rotate, the rail 38 contacts a detent 54 on the inner surface of the finger 50. Contact between the detent 54 and the rail 38 exerts a force on the rail 38 in the direction toward the pin 46. The clamping lever 44 continues to rotate relative to the pin 46 such that the detent 54 passes across the rail 38 and the rail 38 is received into a pocket 58 adjacent to the detent 54. The detent 54 prevents the clamping lever 44 from rotating back in a direction opposed to the direction R, such that the clamping lever 44 holds the rail 38 firmly. Additionally, the radius of the inner surface 56 of the finger 50 relative to the pin 46 may be less at the pocket 58 then at the end of the finger 50. The rail 38 and the pin 46 are thus pressed together. Because the pin 46 is connected to the first arm 22, the first arm 22 is pressed downward toward the rail 38, and thus pressed into the second arm 24 to ensure firm and secure engagement. The pocket 58 is shaped such that the clamp 20 may still translate along the rails 38 even after the arms 22, 24 are securely clamped together. After the pocket 58 has received the rail 38, the clamping lever 44 may be characterized as being in a locked configuration. The clamping lever 44 may be constructed such that, in the locked configuration, the interface structure 48 contacts or moves into proximity to the surface of the clamp 20.

A handle 60 is configured to move the clamps 20 closer to one another along the jig 36. After the tissue structures 2, 4 have been clamped down in the clamps 20 and the flaps 8 have been secured by the clips 34, as described above, the user may actuate the handle 60. The handle 60 may be any structure, mechanism or combination thereof that is capable of moving the clamps 20 together along the jig 36. As one example, each clamp 20 is connected to a leg 62 of the handle 60. The legs 62 are connected to one another via a pin 64 or other structure or mechanism. The legs 62 are free to pivot about the pin 64. The handle 60 may include one or more user interface features 66 such as grips. These user interface features 66 may be engaged by hand, by forceps, or by other user input. Alternately, the handle 60 may be shaped differently, or have different or additional components. Alternately, the handle 60 is not used. For example, the clamps 20 may be moved together manually, such as by hand or by forceps. As another example, the clamps 20 may be biased together, such that removal of a stop (not shown) or other structure allows the clamps 20 to move together along the jig 36 without the use of a handle 60. Additional or different structures and/or mechanisms may be used to bring the clamps 20 together along the jig 36.

Figure 7:
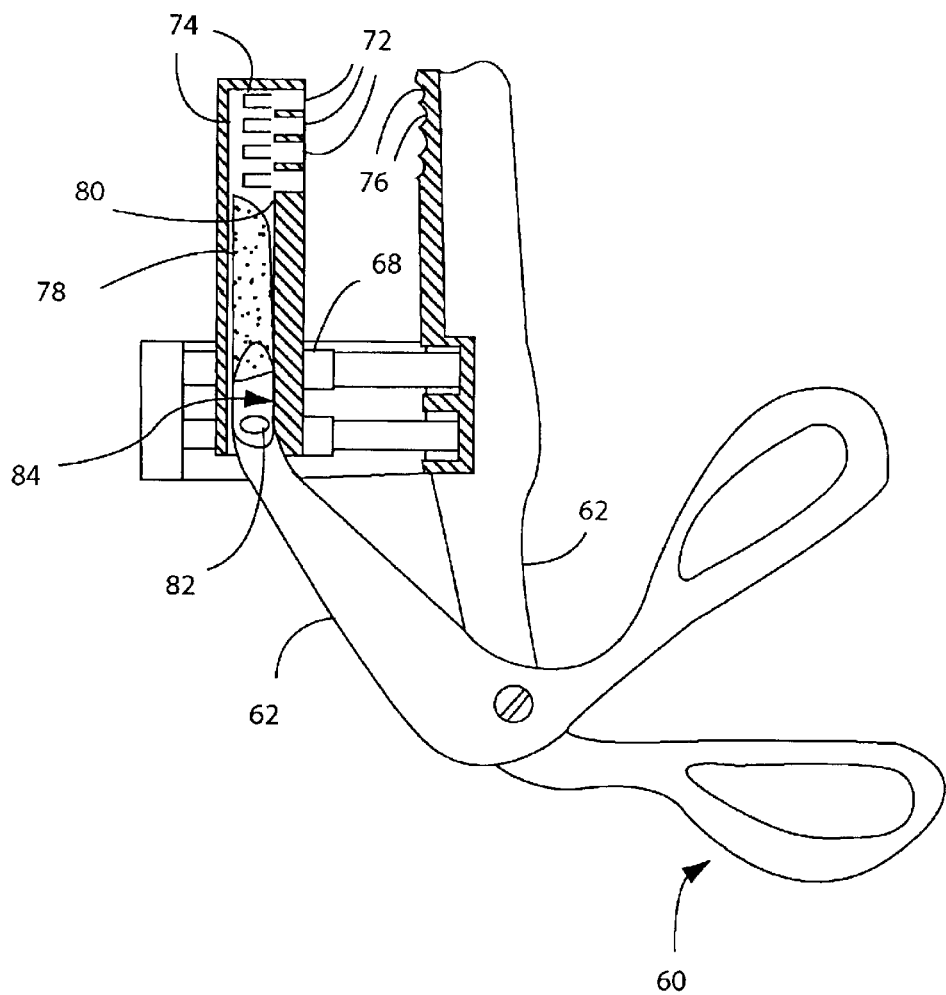
FIG. 7 is a top, partially cut-away view of the anastomosis tool of FIG. 6.

To perform anastomosis between the tissue structures 2, 4, the user actuates the handle 60, squeezing the proximal ends of the legs 62 closer together. The legs 62 begin to pivot relative to one another about the pin 64, thereby causing the distal ends of the legs 62 to move closer together. The motion of the legs 62 closer together causes the clamps 20 to move closer together along the rails 38 of the jig 36. The legs 62 are mounted to the clamps 20 in such a way as to translate the clamps 20 smoothly along the rails 38. A linkage (not shown) or a flexible segment may be used at the interface between at least one leg 62 and the corresponding clamp 20. In this way, the radius of travel of the distal end of at least one leg 62 relative to the pin 64 is converted to substantially linear motion of the corresponding clamp 20. Alternately, a cam mechanism or other mechanism may be used to produce the same substantially linear motion of the clamp 20 from the actuation of the handle 60. Referring also to FIG. 7, one leg 62 may be mounted to a clamp 20 that is fixed to the jig 36, so that it does not translate along the rails 38. Thus, that clamp 20 remains substantially stationary relative to the jig 36, and no linkage or flexible segment is needed to connected that leg 62 to the clamp 20. Alternately, that clamp 20 is not fixed to the jig 36 and the pin 64 is positioned substantially along the longitudinal centerline of that clamp 20.

Optionally, at least one alignment boss 68 is defined on or connected to at least one clamp 20. Each alignment boss 68 is a substantially cylindrical structure extending outward from the contact surface 37 of the first arm 22 of one clamp 20 toward the first arm 22 of the other clamp 20. However, one or more of the alignment bosses 68 may be shaped differently. Advantageously, two alignment bosses 68 are provided on the first arm 22 of one clamp 20. The other clamp 20 includes at least one corresponding boss receiver 70. Each boss receiver 70 is shaped to correspond to the shape of the outer surface of each alignment boss 68. Thus, where the alignment bosses 68 are substantially cylindrical, the boss receivers 70 are substantially cylindrical depressions, each having a diameter slightly larger than the outer diameter of the corresponding alignment boss 68. As each alignment boss 68 is received into the corresponding boss receiver 70, the close fit therebetween causes the two clamps 20 to align more closely. In this way, the distal ends 26, 28 of each clamp 20 are brought into close alignment with the distal ends 26, 28 of the corresponding clamp 20. Thus, the flaps 8 are registered together as they are brought into contact with one another. Alternately, at least one alignment boss 68 is positioned on the second arm 24 of at least one clamp 20 such that one of the rails 38 extends through the lumen of the alignment boss 68. Thus, the outer diameter of the alignment boss 68 is larger than the diameter of the rail 38. Alternately, rather than being tubular structures, the alignment bosses 68 are shaped differently, while still having a lumen therethrough to accept the rail 38. Alternately, each clamp 20 includes an alignment boss 68, where each alignment boss 68 is associated with a different rail 38.

In another embodiment of the tool 30, the jig 36 is not used. Rather, each clamp 20 is connected to a leg 62 of the handle 60. Alignment and registration of the clamps 20 relative to one another is provided by at least one alignment boss 68 and corresponding boss receiver 70. Thus, when the clamps 20 approach close enough to one another, each boss receiver 70 receives the corresponding alignment boss 68. As described above, the interface between each alignment boss 68 and corresponding boss receiver 70 aligns and registers the clamps 20 relative to one another. Where the jig 36 is not used, the arcuate motion of the distal end of each leg 62 of the handle 60 need not be converted to linear motion along the jig 36. In this way, construction of the tool 30 may be simplified.

Referring also to FIG. 5A, motion of the handle 60 and the clamps 20 stops when the flaps 8 contact one another, and the clamps 20 thus cannot move substantially closer to one another. This configuration of the anastomosis tool 30 may be referred to as the deployment position. In the deployment position, the contact surfaces 37 may be spaced apart from each other a small distance, due to the thickness of each flap 8. Alternately, the contact surface 37 of one clamp 20 may contact the contact surface 37 of the other clamp 20. The clamps 20 are not affirmatively locked together; rather, continued actuation of the handle 60 holds the clamps 20 together after the flaps 8 contact one another. Alternately, a locking mechanism (not shown) holds the clamps 20 together after the flaps 8 are brought into contact with one another. The locking mechanism may be a component of one or more clamps 20, of the jig 36, or may be a separate component used to hold the clamps 20 together.

In the deployment position, the flaps 8 are in a mating configuration. That is, each flap 8 on the first tissue structure 2 is pressed against a corresponding flap 8 on the corresponding tissue structure 4. Where the tissue structures 2, 4 are blood vessels, the mating surface of each flap 8 is a portion of the intimal lining of that blood vessel, and the flaps 8 are pressed together such that their intimal surfaces contact one another. After the flaps 8 are brought together, they are connected to one another. At least one clamp 20 includes one or more connector deployers 72. The connector deployers 72 are structures or mechanisms for deploying connectors 74 into the flaps 8 to connect them together. The connectors 74 are staples. Alternately, the connectors 74 are any other connectors, fasteners, structures or mechanisms useful for connecting the flaps 8 of the first tissue structure 2 to the flaps 8 of the second tissue structure 4. One example of a connector deployer 72 is an opening in a clamp 20, with a connector 74 held adjacent to that opening, such as by a friction fit. Other mechanisms may be used as connector deployers 72. A connector receiver 76 may be provided opposite one or more of the connector deployers 72 on the other clamp 20. For example, if the connectors 74 are staples, then the connector receivers 76 are staple-forming surfaces configured to bend the staples into a configuration in which they hold mating flaps 8 together. The connector receivers 76 may be shaped differently, and may be omitted altogether, depending on the characteristics of the connector 74 that is utilized. Advantageously, connector deployers 72 are provided in a single clamp 20, in order to simplify their actuation. However, connector deployers 72 may be placed in more than one clamp 20, if desired. Referring also to FIGS. 1 and 5, connector deployers 72 are located on each arm 22, 24 of at least one clamp 20. By providing connector deployers 72 on each arm 22, 24, connectors 74 can be deployed around the lumen 10 of each tissue structure 2, 4. That is, connectors 74 can be deployed through the flaps 8 of the tissue structures 2, 4 such that they are placed substantially evenly around the circumference of the lumen 10 of each tissue structures 2, 4. Alternately, the connector deployers 72 can be positioned differently within the arms 22, 24 of at least one clamp, as long as such a position allows the flaps 8 to be connected together securely and substantially without leakage. Alternately, the connector deployers 72 do not deploy physical connectors, but rather apply energy or otherwise manipulate the flaps 8 to connect them. Such connector deployers 72 may be tissue-welding electrodes, waveguides, or mechanisms for delivering adhesive.

Referring to FIG. 7, at least one actuator 78 is connected to at least one leg 62 of the handle 60. Each actuator 78 is constrained to move within a channel 80 within each arm 22, 24 in which connector deployers 72 are placed. After the flaps 8 of the tissue structures 2, 4 have been brought together, at least one leg 62 continues in its motion, or otherwise causes the actuator 78 to move. The actuator 78 is a piece of material that fits within the channel 80, and which is shaped at its distal end in such a way as, when it is urged distally, to cause the connector deployers 72 to deploy connectors 74. As one example, the distal end of the actuator 78 is curved or angled relative to connectors 74 that extend at least partially into the channel 80 before they are deployed. In this example, the connector deployers 72 are simply passages between the channel 80 and the contact surface 37 of the clamp 20. As the leg 62 continues to move as the handle 60 is compressed, the leg 62 urges each actuator 78 distally along the channel 80. The distal end of each actuator 78 engages each connector 74 in the arm 22, 24, serially pushing each connector 74 out of the channel through the corresponding passage of the connector deployer 72. As the distal tip of the actuator 78 passes by each connector deployer 72, the full width of the actuator 78 passes through the channel 80 and presses against the connector 74, forcing it out of the connector deployer 72. Where the connectors 74 are staples, this force presses the connectors 74 against corresponding connector receivers 76, causing them to bend and thus connect the mated flaps 8 together. Other actuators 78 may be used instead. Further, where connector deployers 72 are provided in more than one clamp 20, an actuator 78 is provided in each clamp 20. The actuators 78 need not have the same configuration or construction in each clamp 20.

As described above, at least one leg 62 may includes a linkage or flexible portion to allow the end of the leg 62 to rotate through an arc relative to a pin 64 while at the same time translating the connected clamp 20 in a linear direction. As seen in FIG. 7, such a linkage may include a pin 82 connected to the leg 62, where that pin 82 is moveable through a slot 84 in the clamp 20. When the clamps 20 are pressed together, the leg 62 continues to move, continuing to urge the pin 82 along the slot 84, where that pin 82 engages the actuator 78 and causes the connectors 74 to deploy. The linkage or flexible element connecting the leg 62 to the clamp 20 may be configured to allow the pin 82 to move along the slot 84. Alternately, an additional linkage or element may be provided to allow the pin 82 to move along the slot 84 as the handle 60 continues to be compressed or otherwise actuated. Thus, a continued smooth motion of the handle 60 brings the flaps 8 of the tissue structures 2, 4 together and deploys the connectors 74 into them.

Figure 8:
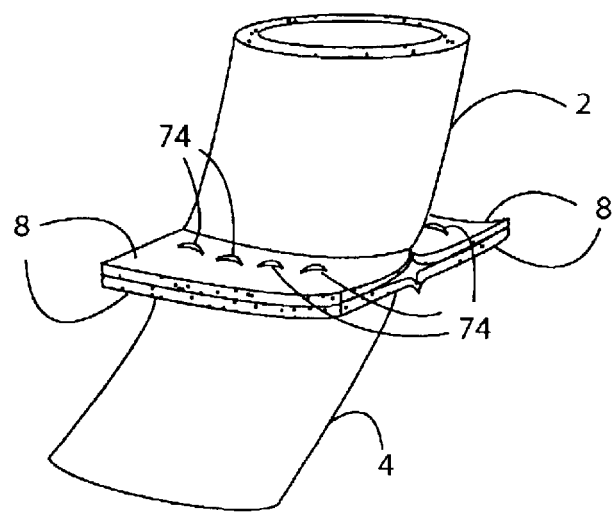
FIG. 8 is a perspective view of a completed end-to-end anastomosis.

After the connectors 74 have been deployed, the tissue structures 2, 4 are connected together, as shown in FIG. 8. The flaps 8 of the first tissue structure 2 have been connected to the flaps 8 of the second tissue structure 4 with at least one connector 74. As shown in FIG. 8, a number of connectors 74 have each penetrated one flap 8 of the first tissue structure 2 and an abutting flap 8 of the second tissue structure 4. Advantageously, the connectors 74 are spaced apart from one another a distance comparable to the distance between stitches in a sutured anastomosis. The flaps are then freed from the clips 32. A tissue knife (not shown) may be used in conjunction with each clip 32 to free the associated flap 8, as well as to cut excess flap tissue away from the anastomosis. Each tissue knife is a cutting structure or mechanism that does not engage the flaps 8 until the connectors 74 have been deployed. As each actuator 78 is urged distally, it engages the corresponding tissue knife, such that the actuator 78 causes the tissue knife to cut through the flaps 8, cutting the flaps 8 completely free of the clips 32 after the connectors 74 have all been deployed. As one example, a slot (not shown) on the contact surface 37 of each clamp 20 is located under each flap 8, and a tissue knife is deployed out of and along each such slot in order to cut the corresponding flap 8. Alternately, a structure or mechanism other than the actuator 78 may be used to activate the tissue knives. Alternately, the tissue knives are not used, and a forceps or other tool is used to lift the clips 32 from their closed positions and free the flaps 8.

Referring also to FIG. 5, a passage 86 optionally may be defined through the contact surface 37 of each arm 22, 24. A finger (not shown) extends through adjacent pairs of passages 86. The finger transmits the motion of the actuator 78 or other mechanism from one arm 22, 24 to the adjacent arm 22, 24 in the other clamp 20 in order to actuate the tissue knives in that clamp 20. That is, motion of each actuator 78 is transmitted to a corresponding finger, which moves through the corresponding passage 86 in one arm 22, 24 to actuate the corresponding tissue knife in the other arm 22, 24. Alternately, the passages 86 are not provided, and the tissue knives in the other clamp 20 are actuated with a mechanism within that clamp 20. The clamping levers 48 are then rotated out of their locked configuration, and the arms 22, 24 of each clamp 20 separate to allow the connected tissue structures 2, 4 to be freed easily from the tool 30.

Although the tool above has been described in the context of microvascular anastomosis, the tool also may be used to perform end-to-end anastomosis between hollow tissue structures other than small-diameter blood vessels, such as larger blood vessels, intestinal segments, ducts such as the bile duct, and other hollow tissue structures. The tool may also be used to perform end-to-end connections between solid tissue structures such as muscles, tendons and nerves, particularly solid tissue structures having a small cross-section. Flaps can be created at the end of such solid structures as described above, and those solid structures can be connected end-to-end by those flaps in the same manner as described above. Additional or different fasteners may be used to connect such flaps to ensure that the solid structures are firmly connected to one another.

While the invention has been described in detail, it will be apparent to one skilled in the art that various changes and modifications can be made and equivalents employed, without departing from the present invention. It is to be understood that the invention is not limited to the details of construction and/or the arrangements of components set forth in the above description or illustrated in the drawings. Therefore, the invention is not to be restricted or limited except in accordance with the following claims and their legal equivalents.

What is claimed is:

1. A tool for performing end-to-end anastomosis between a first tissue structure and a second tissue structure each having at least two flaps at one end, comprising:

a first clip configured to hold at least one flap of the first tissue structure, wherein said first clip is movable between an opened position and a closed position in which said first clip compresses the flap, a second clip configured to hold at least one flap of the second tissue structure, wherein said second clip is movable between an opened position and a closed position in which said second clip compresses the flap, wherein said clips are movable from a first position spaced apart from one another to a second position closer to one another in which each flap held by said first clip abuts a corresponding flap held by said second clip; and at least one connector deployer oriented to deploy at least one connector completely through at least one of two abutting flaps.

2. The tool of claim 1, further comprising a first clamp configured to hold the first tissue structure, and a second clamp configured to hold the second tissue structure; wherein said first clip is connected to said first clamp and said second clip is connected to said second clamp.

3. The tool of claim 2, further comprising a jig, wherein each said clamp is connected to said jig.

4. The tool of claim 3, wherein at least one said clamp is fixed to said jig.

5. The tool of claim 3, wherein said jig comprises at least one rail, and at least one said clamp is slidably connected to at least one said rail.

6. The tool of claim 3, further comprising a handle connected to each clamp, wherein said handle is configured to urge at least one said clamp relative to said jig.

7. The tool of claim 3, wherein one said clamp further comprises at least one alignment boss, and wherein the other said clamp comprises at least one boss receiver defined therein.

8. The tool of claim 7, wherein each said alignment boss is substantially tubular.

9. The tool of claim 2, wherein at least one clamp comprises an actuator configured to actuate at least one said connector deployer.

10. The tool of claim 9, further comprising a channel defined in at least one said clamp, wherein said actuator is movable through said channel relative to at least one said connector deployer.

11. The tool of claim 2, wherein a first clamp comprises at least one connector deployer, and a second clamp comprises at least one connector receiver corresponding to said connector deployer on said first clamp.

12. The tool of claim 2, wherein each clamp comprises a first arm and a second arm moveable between an open position and a closed position.

13. The tool of claim 12, further comprising a clamping lever movably connected to at least one said clamp, wherein motion of said clamping lever to a predetermined position locks said first arm and said second arm into said closed position.

14. The tool of claim 2, wherein each clamp comprises a passage defined therein; further comprising a finger moveable between said clamps through said passages.

15. The tool of claim 2, wherein each said clamp further comprises at least one tissue knife configured for cutting at least one flap.

16. The tool of claim 1, wherein at least one said connector is a staple.

* * * * *